(12) United States Patent
Heinrich et al.

(10) Patent No.: US 6,866,846 B1
(45) Date of Patent: Mar. 15, 2005

(54) PATIENT-SPECIFIC IMMUNOADSORBERS FOR THE EXTRACORPOREAL APHERESIS AND METHODS FOR THEIR PREPARATION

(75) Inventors: Hans-Werner Heinrich, Riemserort (DE); Wolfgang Ramlow, Bad Doberan (DE); Hans-Friedrich Boeden, Berlin (DE); Hans-Georg Neumann, Rostock (DE); Udo Meyer, Hastorf (DE); Joachim Teller, Güstrow (DE)

(73) Assignee: Privates Institut Bioserv GmbH, Rostock (DE)

( * ) Notice: Subject to any disclaimer, the term of this patent is extended or adjusted under 35 U.S.C. 154(b) by 0 days.

(21) Appl. No.: 09/054,888

(22) Filed: Apr. 3, 1998

Related U.S. Application Data (63) Continuation of application No. PCT/DE96/01910, filed on Oct. 3, 1996.

(30) Foreign Application Priority Data

Oct. 5, 1995 (DE) .......................................... 195 38 641

(51) Int. Cl.$^7$ ........................ A61K 39/00; C07K 1/14; G01N 33/564
(52) U.S. Cl. .................... 424/140.1; 436/507; 436/824; 530/412; 530/413; 530/415; 530/416; 530/868; 604/5.01; 604/5.02
(58) Field of Search ...................... 424/140.1; 436/824, 436/507; 530/412, 413, 868, 415, 416; 604/5, 6, 5.01, 5.02

(56) References Cited

U.S. PATENT DOCUMENTS 3,964,467 A * 6/1976 Rose ........................ 424/140.1
4,551,435 A   11/1985 Liberti et al. ............... 436/541

FOREIGN PATENT DOCUMENTS

WO    WO 86/07152    12/1986

OTHER PUBLICATIONS

Sueoka, "Present Status of Apheresis Technologies, Part 3: Adsorbent", Therapeutic Apheresis, 1, 271–283, 1997.*
C. Bruneau et al.: Evidence for a Disease Specific Antigen, etc., Clin. Exp. Immun., 53 (1983), pp. 529–535.
P. C. Dau: Plasmapheresis in Acute Multiple Sclerosis, J. Clin. Apheresis, 6, 1991, pp 200–204.
H. H. Euler et al.: A Randomized Trial of Plasmapheresis, etc., Int. J. Artif. Organs, 14, 1991, pp. 639–646.
D. C. Hess et al.: Thrombotic Thrombocytopenic Purpura in Systemic Lupus Erythematosus. etc., J. Rheumat. 19, 1992, pp. 1474–1478.
R. T. Baldwin et al.: Guillain–Barré Syndrome After Heart Transplantation; J. Heart & Lung Trnsplt., 11, 1992, pp. 817–819.
J. Sany: Early Approaches to Immunotherapy of Rheumatoid Arthritis, Eur.J. Rheumatol. Inflam., 11 (1991) pp. 139–147.
K. Korinthenberg et al.: Verlaufscharacteristik und Therapeutische Möglichkeiten, Monatschr. Kinderheilk., 140, 1992, pp. 792–798.
T. Pullar: Combination Therapy in Rheumatoid Arthritis, and J. Braun et al.: Severe Lupus Crisis, etc., both in Letters to Editor, Brit.J.Rheumatol 30, 1991 311–313.

* cited by examiner

*Primary Examiner*—David Saunders
(74) *Attorney, Agent, or Firm*—Goodwin Procter LLP (57) ABSTRACT

A process for preparing a patient-specific immunoadsorber, which comprises (i) extracting a body fluid from a patient having an immunopathological condition, the fluid containing immune complexes that are relevant to that immunopathological condition, (ii) contacting the extracted fluid with an adsorbent for the immune complexes to form adsorbed immune complexes, (iii) eluting the adsorbed complexes to form an eluate, (iv) fractionating the eluate into a plurality of immune complex component fractions, and (v) immobilizing the immune complex components on one or more biologically compatible carriers activated to bond to its surface one or more desired immune complex components.

17 Claims, 5 Drawing Sheets

PATIENT-SPECIFIC IMMUNOADSORBERS FOR THE EXTRACORPOREAL APHERESIS AND METHODS FOR THEIR PREPARATION

RELATED APPLICATION DATA

This application is a continuation, filed under 35 USC 111, of PCT/DE96/01910, filed Oct. 3, 1996, which claims priority to application DE 195 38 641.8, filed Oct. 5, 1995.

FIELD OF THE INVENTION

The invention refers to the preparation of immunoadsorbers on the basis of specific antibodies and/or antigens which, as a result of immunopathological processes, are responsible for causing or maintaining many diseases. This allows a purposeful interference with the immunopathological regulation cycle which is responsible for the clinical consequences without impairing the entire immune system, as it is the case e.g. in the traditional therapy by immunosuppression with drug therapy. The method according to the invention allows, in addition, to enrich and prepare in a pure state immunopathologically relevant endogenic substances, thus opening up new possibilities for investigating the causes and developing therapies.

BACKGROUND

The functional basis of immunoreactions is complex and is based on the well-regulated interaction between local and system-effective cellular and humoral elements of nonspecific defense and the system of specific defense by activated cells of the lymphopoetic system and the mediators and antibodies produced by them.

Depending on the type of stimulation the predominant defense activities can substantially vary.

This augmentation of systemic defense is brought about in a natural way during an infection event or, is produced artificially, such as by drug therapy. This is effected both systematically as well as locally through the respiratory, digestive and urogenital mucosas.

The organism naturally immediately reacts to an infection. The quality and extent of the immediate reaction depends on the type of antigen and the place of invasion. In principle, equal reactions will proceed when giving vaccines or other exogenic substances. A specific defense that is measurable e.g. by the detection of specific antibodies, will become effective only after a few days. After eliminating the triggering cause, the production of specific antibodies will decline and finally will cease. After the biological degradation of antibodies only the presence of specific "memory cells" indicates which antigens the organism had to put up with in the past. Under certain circumstances, particularly in the case of causes which can mostly no longer be determined, the organism reacts hyperactively to endogenic structures. The developing autoimmune reaction results in a continuous destruction of the endogenic tissue the decomposition products of which, in turn, stimulate the immune system. If this pathological regulating cycle is not interrupted the consequences will be finally fatal, at least for the tissue that is involved.

Diseases of an immunopathological genesis or participation are frequently encountered. Due to their chronic course and the difficulties to treat them they strongly affect the quality of the lives of the people involved and cause enormous losses to the economy. One of the autoimmune diseases occurring most frequently is rheumatoid arthritis from which about 1% of the people suffer. This disease manifests itself at about the age of 40. After 10 years approx. 50% of the patients are incapable of earning their livelihood, and 10%–20% of those are most seriously disabled. The results of treatment achieved so far by immunosuppression and supporting therapies are insufficient and frequently end with stopping of the therapy. After 3 years maximally only 50% of the patients treated initially with basic therapeutical agents are still under effective medication.

Due to the frequent insufficient efficacy and large scale side effects of the traditional suppressive therapy, the search continues for new therapeutical methods for treating autoimmune diseases. (J. Sany: Early Approaches To Immunotherapy of Rheumatoid Arthritis. Eur-J-Rheumatol-Inflam: 11 (1991), 139 û 147).

The aim of these therapies is to affect humoral and cellular immune mechanisms as well as mediator systems. Here, experimental attempts showed first successes in animal experiments and clinical testing. However, so far it was not possible to achieve a decisive breakthrough in prognosticating and effectively treating autoimmune diseases of patients.

Immunopathological participation plasma exchange and plasma sorption were successfully applied for a multitude of autoimmune diseases and diseases (R. T. Baldwin, R. R. Pierce and O. H. Frazier: Guillain-Barre Syndrome After Heart Transplantation. J-Heart-Lungtransplany.: 11 (1992), 817–819; J. Braun, J. Sieper, A. Schwarz, F. Keller, J. Heitz and H. V. Ameln: Severe Lupus Crisis With Agranulocytosis and Anuric Renal Failure Due to a Mesangial Lesion (WHO IIB) û successful treatment with cyclophosphamide pulse followed by plasmapheresis (2). Br-J-Rheumatol: 30 (1991), 312–313; P. C. Dau: Plasmapheresis in Acute Multiple Sclerosis: Rationale and Results. J-Clin-Apheresis: 6 (1991), 200–204; H. H. Euler, J. O. Schroeder, R. A. Zeuner and E. Treske: A Randomized Trail of Plasmapheresis and Subsequent Pulse Cyclophosphamide in Severe Lupus: Design of the LPSG Trial. Int-J-Artif-Organs: 14 (1991), 639–646; D. C. Hess, K. Sethi and E. Awad: Thrombotic Thrombocytopenic Purpura in Systemic Lupus Erythematosus and Antiphospholipid Antibodies: Effective Treatment With Plasma Exchange and Immunosuppression. J-Rheumatol: 19 (1991), 1474–1478; R T. Korinthenberg and M. Sauer: The Gullian-Barre Syndrome in Childhood. Clinical Course and Therapeutic Measures. Monatsschr-Kinderheilkd: 140 (1992), 792–798).

Plasma exchange is one of the oldest therapeutic methods, with separated plasma (membrane plasmapheresis or centrifugation) being rejected and simultaneously substituted by donor plasma or human albumin. During a treatment the simple up to a double quantity of the plasma of a patient is exchanged. This method is not selective. To remove one or a few pathogenically important components, the entire plasma of the patient is exchanged and substances which are essential to the patient are rejected. This has serious consequences for the patient which are attempted to be treated by various substitution therapies. In addition, the danger arises of transmitting pathogens such as FIIV or the hepatitis pathogen.

In plasma sorption the initially separated plasma is directed through adsorber material. Substances bonding to certain plasma components are coupled to the absorber material, thus removing them from the patient s plasma. If plasma sorption is applied for removing immunologically important substances the method is referred to as immunoadsorption. Depending on the adsorber material used this method has a varying selectivity and specificity. Various ligands and carriers were clinically used for adsorbing immunoglobulin and immune complexes from the separated plasma.

Ligands clinically used in extracorporeal apheresis methods, include staphylococcal protein A, hydrophobic amino acids (tryptophan or phenylalanin), dextran sulfate, aggregated IgG, anti-human IgG, and antigens of blood groups.

Various autoimmune diseases were successfully treated extracorporeal apheresis immunoadsorption, including rapidly progressing glomerulonephretis, focal glomerulosclerosis, systemic lupus erythermatosus, antiphospholipid syndrome, vasculitides; e.g. periarteriitis nodosa, M. Wegener, rheumatoid arthritis, immunological thrombocytopenic purpura, inhibitors against coagulation factors, hyperimmunized or ABO-incompatible prospective transplantate recipients, polymyoisitis, neurological diseases; e.g. Guillain-Barre syndrome, polyneuropathy, amytrophic lateral sclerosis, myastenia gravis, multiple sclerosis.

Medicinal therapy has a number of disadvantages in treating auto immune diseases. Medicinal immunosuppression is non-selective and non-specific. Also new immunological therapies (monoclonal or polyclonal antibodies against activation markers, or receptor structures of immune cells and mediators) nonselectively suppress the immune response and/or induce immunity phenomena in the organism.

The disadvantages of all known apheresis/absorption systems, analogously to medicamentous immunosuppression, have a disadvantage due to their insufficient selectivity. This applies to the method of Balint and Hargreavans (U.S. Pat. No. 4.681.870), immobilizing staphylococcus aureus protein A on appropriate carriers. By this method IgG and IgG complexes are nonspecifically removed from the blood of patients. This refers also to the method of using carrier-coupled non-specific proteins, preferably immunoglobulins of various species, as immunoabsorbents of immune complexes described by Davis (WO 86/07152). By this method immune complexes, yet not the reactive individual components that are constantly newly formed in the case of autoimmune diseases, are eliminated.

Liberti and Pollora (U.S. Pat. No. 4.551.435) describe a method for the elimination of substances and immune complexes from blood by adding specific antibodies of a specific concentration to patient s blood and forming immune complexes with the substance to be eliminated. They are eliminated from the blood by factors such as C1q, rheumatoid factors, Fc receptors, and cells bearing Fc receptors immobilized on a solid carrier. The application of this method presupposes the cause to be known which, however, is not the case in most cases of autoimmune diseases and the causing antigen is required to be available in a purified condition for the production of antibodies. The immune complexes themselves are nonspecifically removed, not through protein A but through biomolecules, which, due to physiological reasons, have a high affinity to immunoglobulins.

The pathophysiologically relevant immunostructures vary in individual automimmune diseases. There is a variation even between the immunity phenomena of one and the same disease. The use of the known apheresis systems does not only result in an elimination of the immunopathologically relevant but also of the physiological immunoglobulins which are, however, essential to endogenic defenses. The result is a general weakening of the immune system with the risk of septic complications.

BRIEF DESCRIPTION OF INVENTION

The present invention is aimed at providing a method of a therapy for patients suffering from diseases which are caused by a dysregulation of the immune system or which through immunopathological processes develop into chronic forms that are otherwise difficult to treat. It is based on the task to provide a specific immunoadsorber for a respective patient by means of which it will be possible to remove pathogenetically important immune complexes, autoantibodies and antigens from the blood or plasma of the patients through adsorption.

A process for preparing a patient-specific immunoadsorber, which comprises extracting a pathologically relevant body fluid such as blood or plasma, containing immunological factors that are relevant to an immunopathological condition such as an autoimmune disease, to be treated from a patient having such a condition, contacting the extracted fluid with an adsorbent for the immunological factors contained in the fluid to absorb the immunological factors, eluting the adsorbed components to form an eluate, fractionating the eluate into a plurality of biologically active immune complex component fractions suitably of pH 2–5 or 10–2, optionally followed by one or more salts, and immobilizing pathologically relevant fractions on one or more biologically compatible carriers activated to bond to its surface one or, more desired immune complex components To this end, immune complexes are removed from the plasma of the patient by means of known methods, e.g. protein A immunoadsorbers, and after having been eluted appropriately decomposed into their biologically active components. The components can be separately and individually coupled to an appropriate carrier material applying known methods, e.g. gel chromatography, or coupled thereto as a mixture of antibodies and antigens. Immune complexes, antibodies and antigens important for the disease can be removed specifically from the plasma of the patient by means of plasmapheresis with the aid of these immunoadsorbers. These columns can be reactivated and are envisaged as for multiple use. Such patient-specific immunoadsorbers can generally be prepared for all diseases in wh autoimmune complexes play a pathogenetic part.

The patient-specific immunoadsorbers of the present invention are antigens and/or antibodies separated from immune complexes of pathologically relevant immune factors of patients bonded to activated solid carrier materials. They contain antigens and/or antibodies separated from patients suffering from diseases which are caused or maintained by dysregulation. Autoimmune diseases or immunopathological states of reaction include, for example, rheumatoid arthritis, rapidly progressing glomerulonephretis, systemic lupus erythermatosus, antiphosphoid syndrome, vasculitides, histoincompatible recipients of transplantates, polymyositis, neurological autoimmune diseases or immunopathological dysregulations as a result of infectious diseases. All biologically compatible substances which are able to bond covalently to their surface sufficient components of immune complexes are suitable as carrier materials. Sepharose and pearl cellulose are particularly suitable.

The patient-specific immunoadsorbers are prepared by first removing immune complexes from the plasma of patients by non-selective methods, such as by protein A immunoadsorbers, and after elution they are decomposed into their biologically active components. The components can be separately or individually coupled to an appropriate carrier material, or as a mixture of antibodies and antigen, by applying known methods, such as gel chromatography. The immune complexes are decomposed into their individual components in an acid or alkaline medium, suitably at pH 2–5 or 10–12 which, if required, after fractionation and, if necessary, after adding salts such as NaCl, MgCl2, LiCl or urea or guadinine hydrochloride to keep the reactants dissociated after reaching a certain concentration, are coupled to solid materials at pH 2–12 by applying conventional methods.

With the aid of these immunoadsorbers it is possible to remove by extracorporeal immunoabsorption from the plasma of the patient his own specific immune complexes, antibodies and antigens that are relevant to the disease. These columns can be reactivated and are envisaged for multiple use. In general, it is possible to produce such patient-specific immunoaborbers for all diseases in which autoimmune complexes play a pathogenetic part.

In addition to being applied in therapy this method allows to isolate substances from the blood of a patient which, at least, have a share in causing the immunological dysregulation. This simplifies the investigations relating to the pathogenesis of autoimmune diseases or diseases intensified in their course by disturbed functions. Its advantage as compared with traditional solutions is:

Not only immune complexes but also individual reactants so far not affected are removed.

A substitution of foreign immunoglobulins is no longer necessary (Transmission of diseases such as HIV is excluded, additional costs are avoided).

Without knowing the cause of the disease patient-specific immunoadsorbers may be prepared at low costs. Thus, specific therapeutical instruments may be provided also for such autoimmune diseases for which, owing to the low sickness rate, purposeful developments by industry are rejected for reasons of costs.

Antigens and/or antibodies which are responsible for causing or maintaining an autoimmune disease of an individual patient may be specifically enriched, isolated and thus provided for further investigations.

DESCRIPTION OF THE FIGURES

The invention is also disclosed with reference to the appended figures, wherein.

DETAILED DESCRIPTION

Patients suffering from autoimmune diseases such as e.g. rheumatoid arthritis, lupus erythermatosus or multiple sclerosis are subjected to an extracorporeal apheresis using staphylococcal protein A immunoadsorbers. Upon conclusion of an apheresis cycle the column is thoroughly washed with a buffer where detergents were added or adsorptively bonded plasma components are removed from the column by an increased ion concentration (e.g. 1–3 mol/l NaCl). The release of adsorptive plasma components is checked by electrophoresis or an immunoassay of the rinsing buffer. Thereupon, immunoglobulins, immune complexes and the dissociated immunological reactants are eluted by means of a pH gradient (e.g. citrate or acetate buffer at pH 7–2) or concentrated salt solutions with a varying pH (between 4 and 7). The eluted fractions are analyzed for their protein spectrum and the degree of dissociation of immune complexes by electrophoresis, chromatography or other appropriate separation processes.

Fractions of the immune complexes split up into their reactive components are used for immobilization on solid carriers. Before being coupled they can be separated, if needed, by applying appropriate separation processes. The components of the immune complex are individually coupled or are coupled as a mixture to carrier materials activated by ONB-carbonate or H-hydroxy succinimide ethyl ester by known methods. After removing all components that are not bonded, a patient—specific and regenerable immunoadsorber is thus provided, with the aid of which only substances responsible for the immunopathological humoral dysregulation can be selectively removed from the blood of a patient.

The following examples illustrate some specific details of the present invention.

EXAMPLE 1

Model Experiments for the Determination of the Biological Activity of Immobilized Human IgG by Bondiny Anti-human IgG (Poat)

Human IgG was coupled to the carriers sepharose 6FF, and pearl cellulose under elution conditions. Cl—CO—ONB activated gel containing approx. 30 µmol of ONB-carbonate groups per ml were used for coupling human IgG. 1 ml of antiserum (5.3 mg of anti-human IgG) were diluted by 1 ml of PBS and applied to the respective carriers at a flow rate of 0.1 ml/min. The columns were washed with a few column volumes of PBS and 3 M of NaCl at pH 5.0. The elution was with 0.1 M of glycine HCl, 0.05% Tween 20 at pH 2.0 and a flow rate of 1.0 at ml/min. at 2–6 Cl. The concentration of protein was spectrophotometrically determined at a wavelength of 280 nm after the eluates were neutralized with 0.5 M of K2HPO4. The relative bonding capacity of antibodies per ml gel is related to the coupling of IgG under standard conditions 0.5 M of phosphate buffer, 0.05% of Tween 20 at pH 7.2.

The eluted and coupled immobilized human IgG with anti-human (goat) IgG antibodies had the following biological activity.

| ONB-activated | coupling conditions | quantity of coupled human IgG mg/ml of gel | anti-human IgG bonding capacity mg antibodies/ ml gel | bonding efficiency of immobilized IgG μg antibodies/ mg IgG | relative carrier activity (%) |
|---|---|---|---|---|---|
| pearl cellulose | 0.5 M of phosphate, pH 7.2 | 2.3 | 4.1 | 1800 | 100 |
| pearl cellulose | 0.5 M of phosphate, pH 7.2 | 6.2 | 4.1 | 660 | 100 |
| pearl cellulose | 0.1 M of citrate, pH 3.0 | 6.2 | 2.2 | 360 | 54 |
| pearl cellulose | 0.1 M of citrate, pH 3.0 | 3.8 | 4.3 | 1100 | 105 |
| pearl cellulose | 4.5 M of MgCl2, pH 6.0 | 1.4 | 2.5 | 1790 | 61 |
| sepharose 6FF | 0.5 M of phosphate, pH 7.2 | 3.5 | 3.2 | 910 | 78 |
| sepharose 6FF | 0.1 M of citrate, pH 3.0 | 1.2 | 2.5 | 2080 | 61 |
| sepharose 6FF a) | 0.1 M of citrate, pH 3.0 | 5.0 | 3.3 b) | 660 | 80 |
| sepharose 6FF a) | 0.1 M of citrate, pH 3.0 | 5.0 | 3.8 c) | 760 | 93 |
| sepharose 6FF | 0.1 M of phosphate, pH 12.0 | 2.8 | 3.2 | 1140 | 78 |
| sepharose 6FF | 4 M of guadinine*HCl | 2.0 | 3.7 | 1850 | 90 | a) activated with Cl-CO-ONB in the presence of tertiary amines (base catalyzed); degree of activation: 20 = mol of ONB-carbonate groups/ml of gel; coupling efficiency: 57%;
b) 53 mg of antibodies purified by affinity chromatography in 9.2 ml neutralized elution buffer; flow rate: 0.1 ml/min; washing buffer: PBS, 3 M of NaCl (pH 5.0); elution at a flow rate of 1 ml/min.; 63% of the antibodies offered were eluted;
c) 5.3 mg of antibodies purified by affinity chromatography in 9.2 ml of neutralized elution buffer; flow rate: 0.1 ml/min; washing buffer: PBS, 3 M of NaCl (pH 5.0); elution at a flow rate of 0.5 ml/min.; 70% of the antibodies offered were eluted.

EXAMPLE 2

Model Experiments for the Determination of the Bonding Capacity of Human IgG (Antigen), Immobilized by Means of Base-activated ONB-carbonate Sepharose 6FF at pH of 3.0 by Affinity Chromatography Using Anti-human IgG (Antibodies) in Excess Human IgG (sigma) was dissolved in the coupling buffer for coupling and filtered at 0.2 μm. This solution was added to the activated sepharose wetted by a solvent. Coupling was effected at room temperature for 1 hour under careful movement. After having been blocked with 1 M ethanolamine in 0.1 M borate at pH 8.0 for 1 hour, the gel was intensively washed, e.g. in a frit always with 10 times of the column volume in the following order: coupling buffer—water—0.01 HCl—water—24 hours with 0.1 borate butter at pH 8.3—water.

Affinity chromatography was carried out at 2–6° C. with the ECONO system (Bio-Rad) using an Omnifit column 5.0×0.3 I.D. and 350 m$\mu$l gel. Flow rates between 0.25 and 1.0 me/min. were chosen. The elution was measured by a UV-flowphotometer (280 nm). After bonding and washing with PBS the antibodies were eluted according to the flowing programme of 30 min PBS, 60 min 3 M of NaCl at pH 5, 30 min. PBS, 60 min. 0.1 M of glycine*HCl at pH 2.0, and 30 min. PBS at a flow rate of 0.25 ml/min.

The bonding capacity of human IgG antigen (ag) by chromatography with an excess of anti-human IgG, is shown in the following table.

| | | ab bonding conditions | | | | bonding capacity | | | |
|---|---|---|---|---|---|---|---|---|---|
| experiment no. | immobilized ag mg/ml gel | ab offered mg/run | ab concentration μg/ml | ratio ab/ag | execution | flow rate ml/min. | PBS washing gel volume | quantity of eluted ab mg/ml gel | %b) 2 ab/ag |
| 1 | 5.0 | 6.2 | 1030 | 2.5 | BA | 3 h RT | \|20 | 10–4 | 104 |
| 2 | 5.0 | — | — | 2.5 | BAE | batch | 3 × 1 h 1 × 60 h \| 400a) | 7.1 | 71 |
| 3 | 5.0 | — | — | 2.6 | BAE | batch | 1 h 1 × 16 h \| 320a) | 7.5 | 75 |
| 4 | 5.0 | 3.1 | 210 | 4.2 | BAL | 0.02 | \|22 | 13.7 | 137 |
| 5 | 5.0 | 4.1 | 1050 | 2.3 | ML | 0.1 | \|22 | 7.1 | 71 |
| 6 | 5.0 | 4.1 | 210 | 2.3 | ML | 0.1 | \|86 | 7.7 | 77 |
| 7 | 5.0 | 5.7 | 300 | 3.3 | ML | 0.02 | \|22 | 11.4 | 114 |
| 8 | 5.0 | 5.6 | 925 | 3.2 | MC | 7 h 0.5 | 2 × 1 h 2 × 16 h \| 200a) | 9.7 | 97 |
| 9 | 5.0 | 7.2 | 210 | 4.1 | MC | 14 h 0.5 | 5 × 1 h 1 × 16 h \| 300a) | 9.7 | 97 |
| 10 | 5.0 | 4.2 | 525c) | 2.4 | MCAC | 6 h 0–5 | 2 × 1 h 1 × 16 h \| 400a) | 9.7 | 97 |

RAT room temperature
BA batch process
BAE Elution of the antibodies bonded in the batch process (1st experiment) after washing with PBS in the column
BAL antibodies offered additionally to the antibodies bonded in the batch process; washing and elution through the column
ML *micro" affinity chromatography with traditional loading by purified antibodies
MC *micro" affinity chromatography with loading of the column by circulation of the purified antibodies
MCAC *micro" affinity chromatography with antiserum, diluted in PBS, by circulation
a)To remove the antibodies offered were washed with PBS in excess and/or adsorptively bonded proteins. Washing was interrupted by a few hourly intervals (or 16 h) before the elution programme was started.

-continued

| | ab bonding conditions | | | | | | bonding capacity | |
|---|---|---|---|---|---|---|---|---|
| experiment no. | immobilized ag mg/ml gel | ab offered mg/run | ab concentration μg/ml | ratio ab/ag execution | flow rate ml/min. | PBS washing gel volume | quantity of eluted ab mg/ml gel | %[b] 2 ab/ag |

[b]The quantity of the anti-human IgG (antibodies) was spectrophotometrically determined at $\gamma_{280}$ ($E^{0.1\%}$ = 1.38) after neutralization with 0.5 M of $K_2HPO_4$. A bonding capacity of 100% is assumed if each immobilized IgG molecule will bond 2 molecules of anti-IgG
[c]antiserum, diluted 1:8 in PBS

EXAMPLE 3

Elution of Anti-HSA (Rabbits) by HSA from Antibody-antigen Complexes Applying HSA-coated Microtitration Plates for the Determination of Optimum Elution Conditions for Affinity Chromatography 96 well microtitration plates were coated with HSA. Each well was incubated with 0.1 μg anti-HSA. Anti-rabbit IgG conjugated with alkaline phosphatase (substrate: 4-nitrophenyl phosphate, (405 nm) served as detection system (ELISA). 200 μl of the respective elution buffer were pipetted into the wells. The elution was effected at room temperature in an hour with the microtitration plate being constantly moved. Anti-HSA was detected after the wells had been thoroughly washed. For the evaluation the average value of the measurements of always 8 wells was formed (% CV=4.4). The percentage of anti-HSA antibodies eluted with PBS was fixed with 0%.

Elution buffer for dissolving the antibody-antigen complexes eluted anti-HSA antibodies (%), with 0.015% Tween 20, is shown below

| | |
|---|---|
| PBS, pH 7.3 | 0 |
| PBS + 1% of SDS, pH 7.3 | 51 |
| 0.10 M of citrate pH 2.5* | 100 |
| 0.10 M of citrate, pH 3.0* | 73 |
| 0.10 M of citrate, pH 3.5* | 27 |
| 0.10 M of citrate, pH 4.0* | 8 |
| 0.10 M of citrate, pH 2.5* | 100 |
| 0.1 M of citrate/phosphate, pH 7.3 | 0 |
| 0.1 M of citrate/phosphate, pH 6.0 | 0 |
| 0.1 M of citrate/phosphate, pH 5.0 | 0 |
| 0.1 M of citrate/phosphate, pH 4.0 | 2 |
| 3.00 M of KSCN, pH 7.3 | 41 |
| 3.00 M of NaCl, pH 5.0* | 0 |
| 3.00 M of guadinine*HCl, pH 7.3 | 66 |
| 4.00 M of guadinine*HCl, pH 7.3 | 90 |
| 6.00 M of urea, pH 7.3 | 7 |
| 0.10 M of borate, pH 11.0 | 35 |
| 0.10 M of phosphate, pH 11.5 | 49 |
| 0.10 M of phosphate, pH 12 | 91 | a) Immobilization of anti-HSA-HSA on base catalyzed, activated ONB-carbonate sepharose 6FF in coupling media used as elution media for immunoaffinity chromatography.

Coupling media with added protein and filtered (0.45 μm), were added to the wet activated ONB-carbonate sepharose 6FF. Coupling was effected for one hour at room temperature under slight movement. Thereupon, blocking was effected for one hour at room temperature with ethanolamine in borate buffer at pH 8.1. The ONB-carbonate groups were spectrophotometrically (max: approx. 267 nm) determined.

0.5 M phosphate buffer, pH 7.3, served to determine the reference value for a maximum immobilization.

Washing was carried out as in the Example 2.

Anti-HSA antibodies were obtained by a preliminary experiment by means of affinity chromatography (0.05–0.1 M of citrate at pH 2.0), neutralized with 0.5 M $K_2HPO_4$, stored at −20° C. and after thawing adjusted to pH 3.0 or 4.0 by diluted HCl for coupling.

HSA was dissolved in PBS, adjusted to the respective pH by diluted HCl and added to the antibody solution to couple the antigen-antibody mixture.

The protein was spectrophotometrically determined at $OD_{280}$ nm (antibodies $E^{0.1\%}$=1.38 and HSA $E^{0.1\%}$=1.67) in the coupling buffer. The immobilized proteins were determined after treating the gels with 1 N NaOH in the supernatant liquid according to Lowry.

The result of coupling (%) is the relative quantity of immobilized protein related to the protein quantity offered.

The immobilization of anti-HSA—HSA is shown in the following table:

| μmol ONB-carbonate groups per ml gel | coupling medium | pH | mg/ml gel offered | protein quantity mg/ml solution | immobil. protein mg/ml gel | result of coupling % |
|---|---|---|---|---|---|---|
| 19.8 | 0.5 M of phosphate | 7.3 | 1.6 A | 0.3 | 1.1 | 70 |
| 31.6 | 0.5 M of phosphate | 7.3 | 3.9 HSA | 3.9 | 1.7 | 43 |
| 5.1 | 0.1 M of phosphate | 7.3 | 1.6 A | 0.3 | 0.6 | 34 |
| 22.3 | elution buffer | 3.0 | 3.2 A | 0.6 | 2.3 | 70 |
| 20.3 | elution buffer | 3.0 | 5.0 D | 1.6 | 3.4 | 67 |
| 10.8 | elution buffer | 3.0 | 3.8 B | 0.5 | 2.3 | 60 |
| 19.8 | elution buffer | 4.0 | 3.8 B | 0.7 | 1.2 | 32 |
| 22.3 | elution buffer | 3.0 | 5.7 C | 0.9 | 2.9 | 50 |
| 19.8 | 4 M of guadinine*HCl | 7.3 | 11.3 B | 11.3 | 4.9 | 43 |
| 22.3 | 0.1 M of phosphate | 12.0 | 4.8 B | 2.0 | 1.3 | 28 |

A anti-HSA
B anti-HSA/HSA 1:1
C anti-HSA/HSA 1:2
D anti-human IgG/human IgG 1:1

EXAMPLE 4

Detection of the Biological Activity (Bondability) of Antigens and Antibodies of the Anti-HSA/HSA Model After Immobilization Under Splitting Conditions for Immune Complexes Given elution conditions (pH 3.0; pH 4.0; 4 M of guadinine*HCl) as described in the $1^{st}$ and $3^{rd}$ examples of execution base catalyzed, activated ONB-carbonate sepharose 6FF was coupled to anti-HSAIHSA. After washing of the column HSA or anti-HSA were offered in the bonding buffer. After repeated washing of the column with PBS the elution (pH 2.0) and photometric determination of the protein concentration were effected.

By these model experiments it was detected that the antigen (HSA) and the antibodies (anti-HSA) from immune complexes (anti-HSAIHSA) immobilized on a carrier under splitting conditions maintain their bondability. The immobilized HSA from immune complexes has always bonded anti-HSA which after repeated elution in ELISA was characterized by a high reactivity to HSA (results were not represented). Assuming that 1 mol of HSA bonds one mol of anti-HSA 0.9 mg of HSA/ml of gel from immune complexes bonding 2.1 mg of anti-HSA were immobilized ($3_{rd}$ experiment). Similar results could be reproduced by the experiments 5, 7, 13 and 16. Anti-HSA (rabbit IgG) immobilized from immune complexes is also efficiently immobilized in this model given standard coupling conditions—the success may be proved by anti-rabbit IgG—yet, coupling is here, obviously, effected in a molecule region resulting in steric hindrances for bonding HSA. The antibodies themselves maintain their biological activity.

The following table summarized the results of Example 2.

| | immobilization conditions[a] | protein offered/ ml gel | concentration µg-/ml | bonding conditions | PBS washing | bonding capacity µg-/ml gel |
|---|---|---|---|---|---|---|
| 1 | 10.8 µmol anti-HSA/HSA 1.1, pH 3 2.3 mg/ml | 3.0 mg HSA | 1055 | 0.3 ml/min, 47 min circulation | 0.028 ml/min, 47 min | 100–200 |
| 2 | 10.8 µmol anti-HSA/HSA 1.1, pH 3 2.3 mg/ml | 13.4 mg HSA | 937 | 0.5 ml/min, 120 min. circulation | 0.5 ml/min. 60 min | 100–200 |
| 3 | 10.8 µmol anti-HSA/HSA 1.1 pH 3 2.3 ml/mil | 3.7 mg anti-HSA | 164 | 0.5 ml/min, 135 min circulation | 0.5 ml/min, 60 min | 2100 (=0.9 mg HSA) |
| 4 | 19.8 µmol anti-HSA, pH 7 1.1 mg/ml | 6.1 mg HSA | 531 | 0.5 ml/min, 120 min circulation | 0.5 ml/min, 60 min | 100–200 |
| 5 | 19.8 µmol anti-HSA/HSA 1.1, pH 4 1.2 mg/ml | 4.2 mg anti-HSA | 368 | 0.5 ml/min, 180 min. circulation | 0.5 ml/min, 60 min | 1211 (=0.5 mg HSA) |
| 6 | 19.8 µmol anti-HSA/HSA 1:1, 4 M of guan 4.9 mg/ml | 8.3 mg HSA | 578 | 0.5 ml/min., 90 min. circulation | 0.5 ml/min., 60 min. | traces |
| 7 | 19.8 µmol anti-HSA/HSA 1:1 4 M of guan. 4.9 mg/ml | 7.1 mg anti-HSA | 470 | 0.5 ml/min, 180 min circulation | 0.5 ml/min, 60 min | 4714 (=2.1 mg HSA) |
| 8 | 19.8 µmol anti-HSA/HSA 1:1, 4 M of guan 4.9 mg/ml | 5.1 mg anti-rabbit IgG | 360 | 0.5 ml/min, 120 min. circulation | 0.5 ml/min, 60 min | 1977 (36%) |
| 9 | 10.8 µmol anti-HSA/HSA 1:1, pH 3 2.3 mg/ml | 5.1 mg anti-rabbit IgG | 360 | 0.5 ml/min, 120 min circulation | 0.5 ml/min, 60 min | 1480 (54%) |
| 10 | 19.8 µmol anti-HSA, pH 7 1.1 mg/ml | 5.1 mg anti-rabbit IgG | 360 | 0.5 ml/min., 120 min. circulation | 0.5 ml/min, 60 min | 2346 (100%) |
| 11 | 22 m/mol anti-HSA, pH 3 2.3 mg/ml | 5.1 mg anti-rabbit IgG | 360 | 0.5 ml/min., 120 min. circulation | 0.5 ml/min., 60 min. | 2246 (48%) |
| 12 | 22.3 µmol anti-HSA, pH 3 2.3 mg/ml | 13.8 mg HSA | 926 | 0.5 ml/min, 120 min circulation | 0.5 ml/min, 60 min | 100–200 |
| 13 | 22.3 µmol anti-HSA/HSA, 1.2, pH 3 2.9 mg/ml | 6.9 mg anti-HSA | 477 | 0.5 ml/min., 120 min circulation | 0.5 ml/min., 60 min | 3580 (=1.6 mg HSA) |
| 14 | 22.3 µmol anti-HSA/HSA, 1:2, pH 3 2.9 mg/ml | 11.2 mg HSA | 784 | 0.5 ml/min., 120 min circulation | 0.5 ml/min, 60 min | 100–200 |
| 15 | 22.3 µmol anti-HSA/HSA, 1.1, pH 12 1.3 mg/ml | 6.8 mg HSA | 600 | 0.5 ml/min, 70 min circulation | 0.5 ml/min, 60 min | 100–200 |
| 16 | 22.1 µmol anti-HSA/HSA, 1:1, pH 12 1.3 mg/ml | 4.4 mg HSA | 424 | 0.5 ml/min, 120 min circulation | 0.5 ml/min, 90 min | 1579 (=0.7 mg HSA) |

[a] indication of µmol active groups per M of gel

EXAMPLE 5

Affinity Chromatography of the Plasma of a Patient Suffering from Lupus Erythematodes (Standard Method)

The plasma of a patient suffering from lupus erythematosus was treated in a protein A column (Pharmacia) for obtaining the total a-globulins. The immobilization of the antibodies was effected through ONB-carbonate activated sepharose 6FF (20 mol/ml).

The following was the compensation of the buffer solutions for immunoadsorption. pH was set by HCl or NaOH, as required.

| | |
|---|---|
| buffer PA, pH 7.0 | 1000 ml |
| trisodium citrate | 3.30 g |
| sodium acetate × 3 $H_2O$ | 5.45 g |
| sodium chloride | 4.90 g |
| disodium hydrogenphosphate | 2.91 g |
| potassium dihydrogenphosphate | 0.26 g |
| eluant PA, pH 2.2 | 1000 ml |
| citric acid × $H_2O$ | 6.12 g |
| sodium chloride | 9.00 g |
| washing buffer 3 M of NaCl pH 7.0 | 1000 ml |
| trisodium citrate | 3.30 g |
| sodium acetate × 3 $H_2O$ | 5.45 g |
| sodium chloride | 175.00 g |
| disodium hydrogenphosphate | 2.91 g |
| potassium dihydrogenphosphate | 0.26 g |
| Tween 20 | 0.50 g |
| citrate buffer 0.1 M, pH 2.2 | 250 ml |
| citric acid | 5.25 g |

A protein A-coupled column (5 ml gel, Pharmacia) was equilibrated with buffer PA. 20 ml high-speed centrifuged, fresh plasma were mixed 1:2 with buffer PA and applied. An Econo system (Biorad) was used for the chromatography. After leaving the column the plasma was applied anew to achieve a complete adsorption. Intensive washing with 5 column volumes of PA was required to remove the material not adsorbed. Nonspecifically bonded proteins were removed by a washing buffer containing 3 M NaCl. The immunoglobulins and proteins were eluted from the immune complexes as a sharp peak by 0.1 M of citrate buffer, 0.05% of TWEEN 20, pH 2.2. The volume of the eluate totalled 6.5 ml. The protein concentration was determined by means of UV-adsorption at 280 nm with 17.6 mg/ml. Immediately after elution igG and proteins available separately were coupled to the ONB-carbonate activated sepharose. For this, 6 ml of the gel prepared according to the manufacturer's instruction and sucked off were added to the eluate and shaken for 1 hour. Due to the buffer effect of the proteins dissolved the eluate has a pH of 3–4. Free bonds had to he saturated by 1 M of ethanolamine in 0.1 M of borate buffer at pH 8.0. By comparing the protein concentrations in the combined washing solutions with the protein A eluate a bonding efficiency of 57% was determined. After thorough washing the gel is available as carrier for affinity chromatographic experiments.

Figure 1:
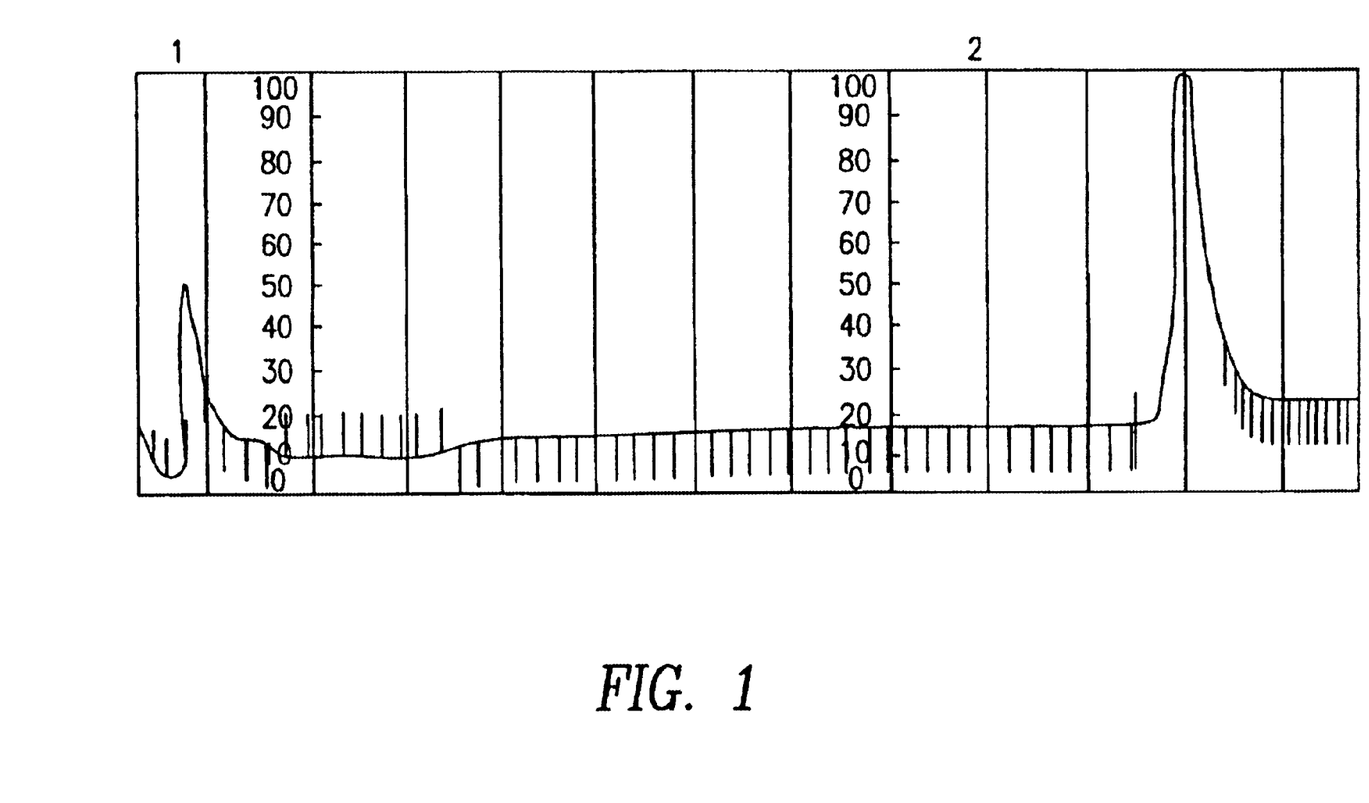
FIG. 1 shows the elution profile of the plasma of a patient after adsorption to sepharose 6FF coupled to homologous antibodies and antigens according to the standard method. The marks give the exchange of buffer during washing and elution (loading of the column is not indicated) wherein I is the washing buffer, 2 is 0.1 M of citrate buffer at pH 2.2.

For this purpose, 40 ml of patient's plasma were centrifuged, diluted 1:2 by PA, and put twice through the column. Non-bonded or non-specifically bonded material were removed by subsequent washing with always 10 column volumes of PA, washing buffer and PA. The specifically bonded protein was eluted by 0.1 M citrate buffer at pH 2.2 as shown in FIG. 1.

The plasma proteins and the chromatographically obtained fractions were analyzed according to standard methods by SDS polyacrylamide gel electrophoresis (SDS-PAGE) (Miniprotean II, BioRad). The gels were gradient gels of 10–25% monomer concentration. Coloring was carried out by coomassie brillant blue R-250 as shown in FIGS. 2 and 3.

Figure 2:
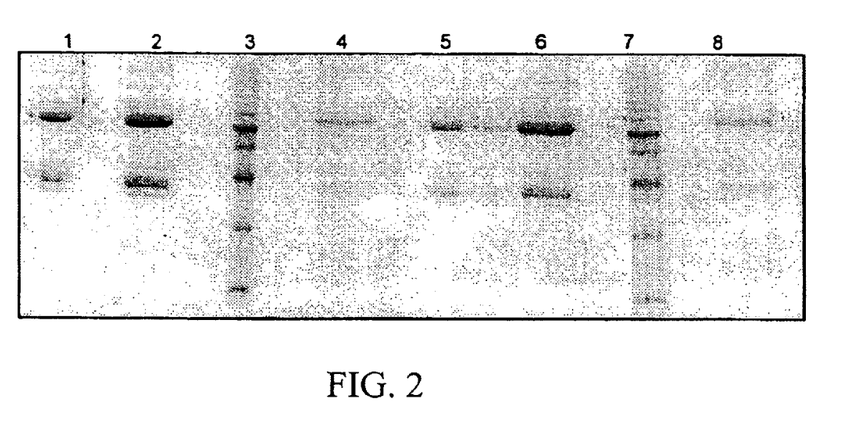
FIG. 2 is a PAGE determination of the eluate from the protein A column before and after coupling to the ONB-carbonate activated sepharose, wherein 1/2 is 5 or 10 µl material before coupling, 3 is 10 kD conductor, 4 is globulin standard, 5–8 are as 1–4, but after coupling (i.e. not bonded material)
Figure 3:
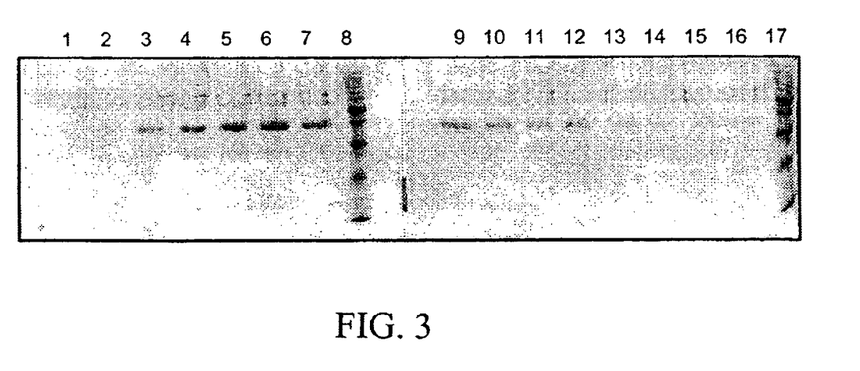
FIG. 3 is a PAGE determination of eluate which was obtained from the immunoadsorbent column at pH 2.2 after passing the homologous plasma, wherein 1–7/9–15 are peak fractions, 8/17 are 10 kD protein marker, and 16 is rinsing.

From FIG. 2 there can be seen that still further proteins are contained in the protein A eluate in addition to antibodies. After their immobilization they are in a position specifically to bond the respective reactants from the patient's plasma. In the elution peak 2 (0.1 M of citrate buffer at pH 2.2) a few proteins were identified in PAGE after affinity chromatography. In addition to immunoglobulins and a few higher molecular proteins 3 proteins, according to PAGE of the protein A eluate detectable only as scarcely visible bands, were decisively enriched as shown in FIG. 3. They show a relative mol mass of about 40 kD.

EXAMPLE 6

Figure 4:
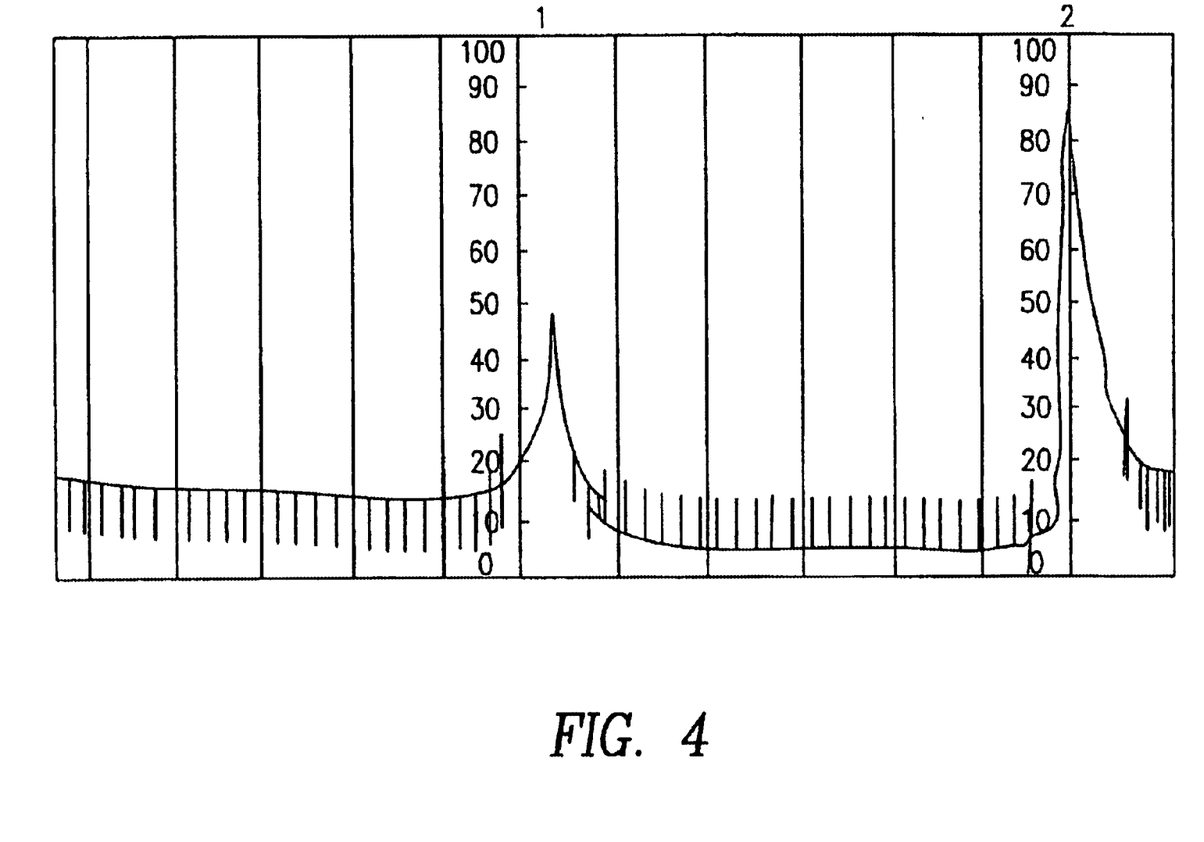
FIG. 4 is an elution profile of the plasma of a patient after adsorption to sepharose 6FF coupled to the homologous antibodies and antigens according to standard methods, the marks give the exchange of buffer during washing and elution (loading of the column is not indicated) wherein 1 is washing buffer, 2 is 0.1 M of citrate buffer at pH 2.2.
Figure 5:
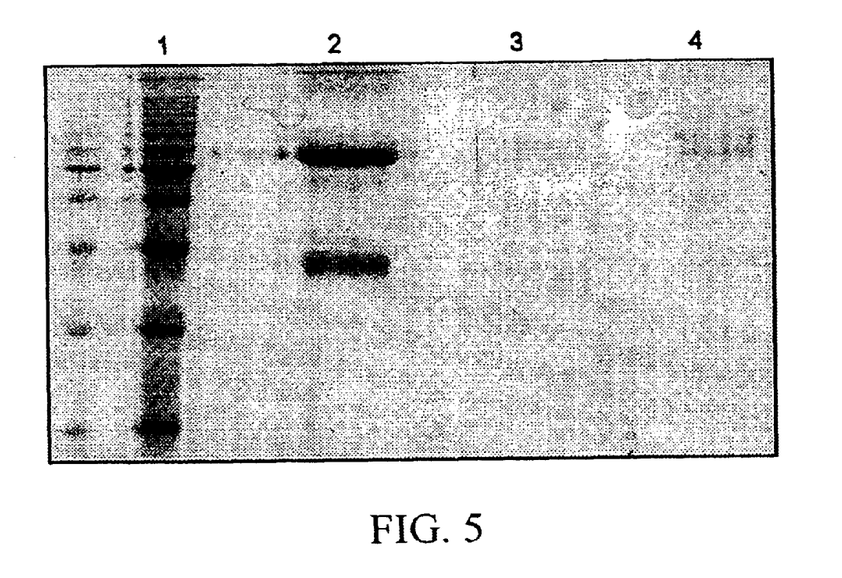
FIG. 5 is a PAGE determination of eluate which was obtained from the immunoabsorbent column at pH 2.2 after passing the homologous plasma, wherein 1 is 10 kD standards, 2 is globulin standard, 3 is peak fraction (peak 2, FIG. 4), and 4 is peak fraction after evaporation through Amicon Centrifree®.

Affinity Chromatography of the Plasma of a Patient Suffering from Multiple Sclerosis The treatment of the plasma, elution of protein A and coupling of the eluate proteins were effected analogously to Example 5. After washing adsorptively bonded proteins from the immunoadsorber (peak 1, FIG. 4) specifically bonded protein is dissolved from the matrix by the elution buffer which, according to PAGE as shown in FIG. 5, proved to be a protein mixture containing mainly immunoglobulins.

EXAMPLE 7

Figure 6:
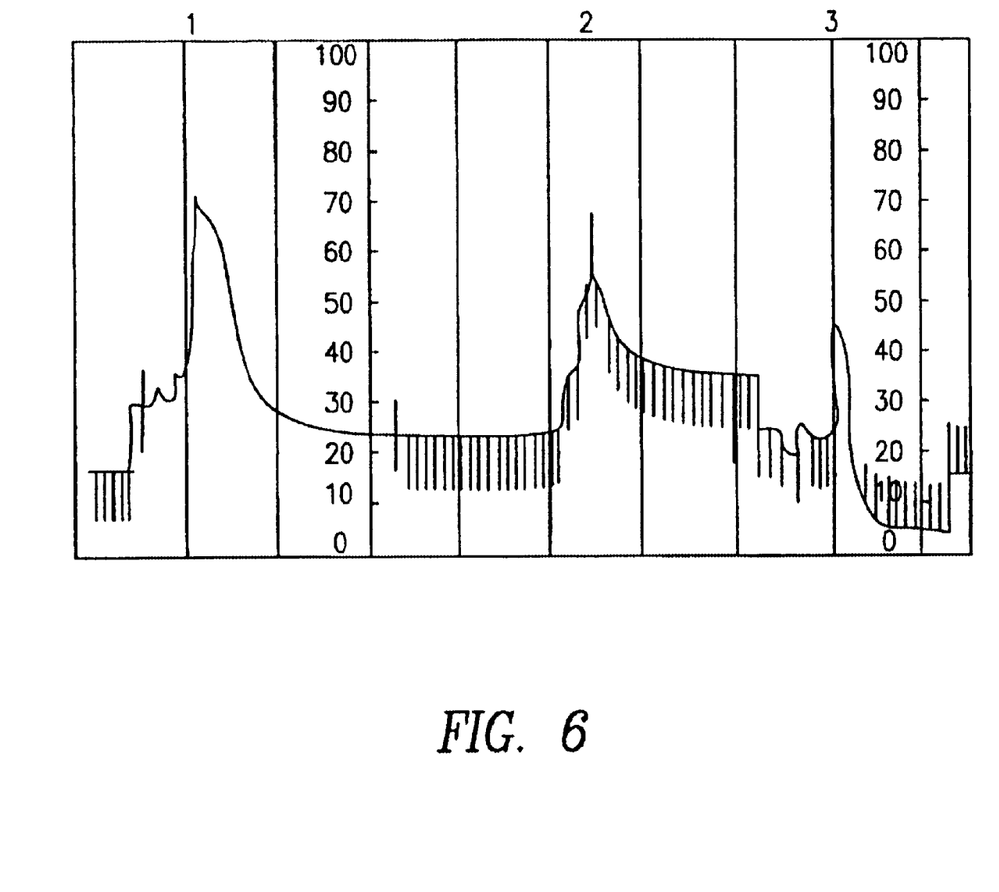
FIG. 6 is an elution profile of the plasma of a patient after adsorption to sepharose 6FF coupled to the homologous antibodies and antigens according to standard methods, the marks give the exchange of buffer during washing and elution (loading of the column is not indicated) wherein 1 is washing buffer, 2 is 0.1 M of citrate buffer at pH 6–0/Tween, and 3 is 0.1 M citrate buffer at pH 2.2.
Figure 7:
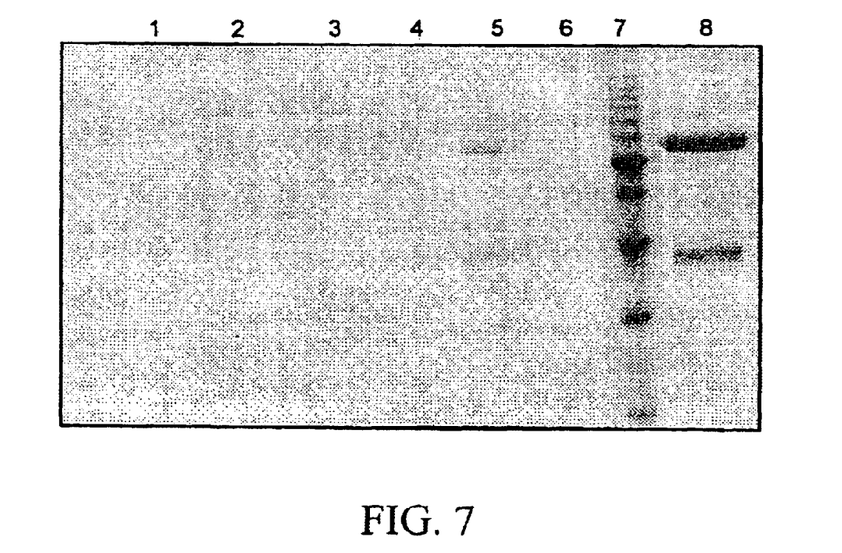
FIG. 7 is a PAGE determination of eluate which was obtained from the immunoadsorbent column at pH 2.2 after passing the homologous plasma, wherein 1–4 are proteins from the washing buffer, 5/6 are peak fractions (peak 3, FIG. 6), 7 are 10 kD standards, and 8 is globulin standard.

Affinity Chromatography of the Plasma of a Patient Suffering from Rheumatoid Arthritis The treatment of the plasma, elution of protein A and coupling of the eluate proteins were effected analogously to Example 5. After washing adsorptively bonded proteins from the immunoadsorber (peak 1, FIG. 6) specifically bonded protein is dissolved from the matrix by the elution buffer which, according to PAGE (FIG. 7), proved to be a protein mixture containing mainly immunoglobulins.

What is claimed is:

1. A process for preparing a patient-specific immunoadsorber, which comprises;
   (i) extracting a body fluid from a patient having an immunopathological condition, the fluid containing immune complexes that are relevant to said immunopathological condition,
   (ii) contacting the extracted fluid with an adsorbent for said immune complexes to form adsorbed complexes,
   (iii) eluting said adsorbed immune complexes to form an eluate,
   (iv) fractionating the eluate into a plurality of immune complex component fractions, and
   (v) immobilizing said immune complex component fractions on one or more biologically compatible carrier materials activated to bond to its surface one or more desired immune complex components.

2. The process of claim 1, wherein said body fluid is blood or plasma.

3. The process of claim 1, wherein said immune complex component fractions comprise an antigen fraction including antigens for said immunopathological condition and an antibody fraction including antibodies against said antigens for said immunopathological condition.

4. The process of claim 1, wherein said eluting is carried out with an elution solution.

5. The process of claim 4, wherein said elution solution comprises glycine HCl.

6. The process of claim 4, wherein said elution solution comprises Tween 20.

7. The process of claim 4, wherein said elution solution comprises NaCl.

8. The process of claim 4, wherein said elution solution comprises PBS.

9. The process of claim 1, wherein said carrier is ONB-carbonate, or H-hydroxysuccinimide-ethylester.

10. The process of claim 1, wherein said immunopathological condition is rheumatoid arthritis, rapid-progressive glomerulonephretis, focal glomerulosclerosis, systemic lupus erythematosus, immunological thrombopenic purpura, antiphospholipid syndrome, vasculitiacs, rejected by histo-incompatible recipients of transplants, polymyositis, neurological disease, or immunopathological dysregulation as a result of infectious disease.

11. The process of claim 10, wherein said vasculitides is periarteritis nodosa, or M. Wegener, and said neurological disease is Guillan-Barre syndrome, polyneuropathy, amylotropic lateral sclerosis, myastheaia gravis, or multiple sclerosis.

12. The process of claim 1, wherein said adsorbent is staphylococcal protein A.

13. The process of claim 1, wherein said adsorbent for said immune complexes is Staphylococcal protein A, a hydrophobic amino acid, or dextran sulfate.

14. The process of claim 13, wherein said hydrophobic amino acid is tryptophan, or phenylalanine.

15. The process of claim 1, wherein said fractionating is carried out at pH 2–5 or 10–12.

16. The process of claim 1, wherein a salt is added after said fractionating.

17. The process of claim 16, wherein said salt is NaCl, $MgCl_2$, LiCl, urea or guanidine HCl.

* * * * *